(12) United States Patent
Ozawa et al.

(10) Patent No.: US 12,279,765 B2
(45) Date of Patent: Apr. 22, 2025

(54) METHOD FOR CLOSING A WOUND

(71) Applicant: OLYMPUS MEDICAL SYSTEMS CORP., Tokyo (JP)

(72) Inventors: Keita Ozawa, Hino (JP); Kunihide Kaji, Hachioji (JP); Hiroyuki Morishita, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 147 days.

(21) Appl. No.: 17/559,144

(22) Filed: Dec. 22, 2021

(65) Prior Publication Data

US 2022/0233190 A1 Jul. 28, 2022

Related U.S. Application Data

(60) Provisional application No. 63/142,592, filed on Jan. 28, 2021.

(51) Int. Cl.
| | |
|---|---|
| *A61B 17/06* | (2006.01) |
| *A61B 17/00* | (2006.01) |
| *A61B 17/04* | (2006.01) |
| *A61M 1/00* | (2006.01) |

(52) U.S. Cl.
CPC .. *A61B 17/06166* (2013.01); *A61B 17/00234* (2013.01); *A61B 17/0057* (2013.01); *A61B 17/0483* (2013.01); *A61M 1/77* (2021.05); *A61M 1/85* (2021.05); *A61B 2017/00269* (2013.01); *A61B 2017/00632* (2013.01); *A61B 2017/00663* (2013.01); *A61B 2017/00818* (2013.01); *A61B 2017/06052* (2013.01); *A61B 2017/06176* (2013.01); *A61B 2217/005* (2013.01); *A61B 2217/007* (2013.01)

(58) Field of Classification Search
CPC ...... A61B 17/0469; A61B 2017/00663; A61B 2017/00269; A61B 1/015; A61B 17/32056; A61B 17/0281; A61B 17/06166; A61B 2017/00358; A61B 2218/002

See application file for complete search history.

(56) References Cited

U.S. PATENT DOCUMENTS

| | | | |
|---|---|---|---|
| 2017/0245842 A1* | 8/2017 | Ito ...................... | A61B 1/00137 |
| 2019/0290325 A1* | 9/2019 | Goto .................. | A61B 17/3478 |
| 2020/0281619 A1* | 9/2020 | Ryan, Jr. ............ | A61B 18/1485 |
| 2021/0162107 A1* | 6/2021 | Kharkar ................ | A61M 1/964 |

* cited by examiner

*Primary Examiner* — Sarah A Long
*Assistant Examiner* — James R McGinnity
(74) *Attorney, Agent, or Firm* — Morgan, Lewis & Bockius LLP

(57) ABSTRACT

A method for resecting a lesion in a wall of an organ of a patient includes injecting a fluid into the wall of the organ at a location proximate to the lesion, creating a wound in the wall of the organ by cutting the lesion from the wall of the luminal organ, removing at least a portion of the fluid injected into the wall of the organ, and closing the wound using a suture thread. The portion of fluid may be removed prior to or after partially threading the suture thread into the wall of the organ.

21 Claims, 7 Drawing Sheets

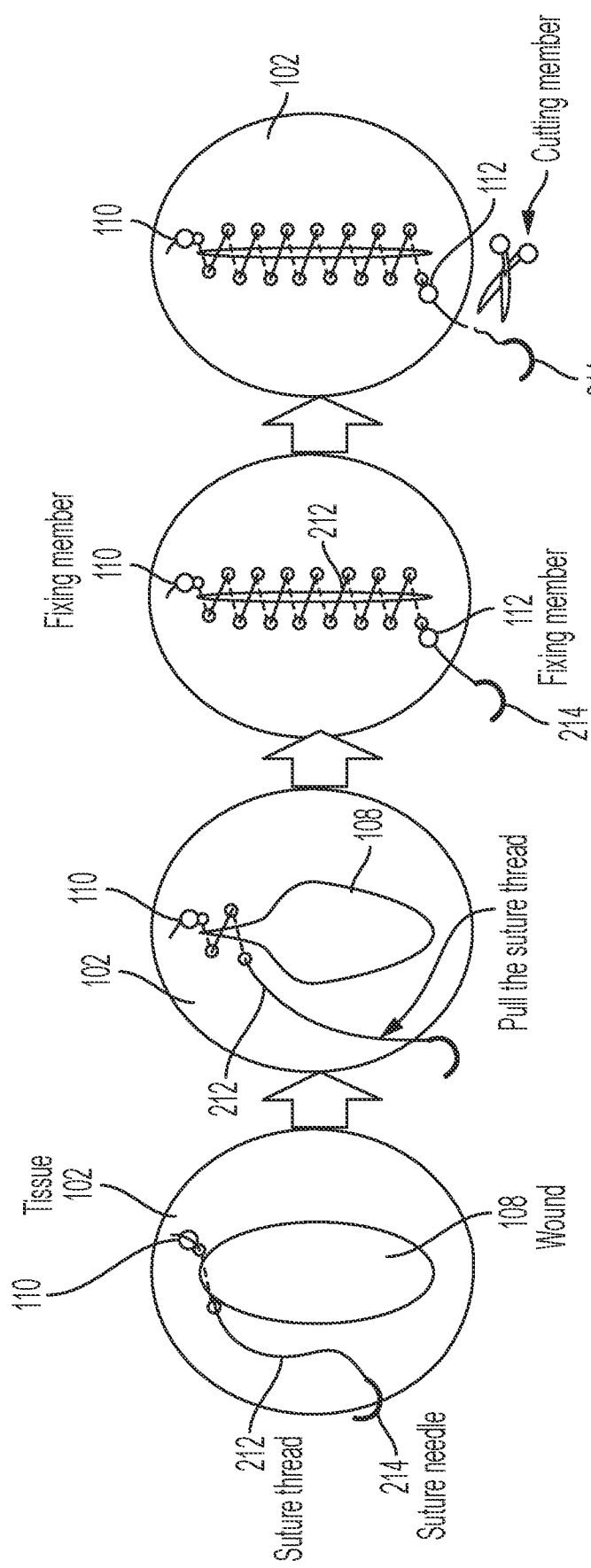

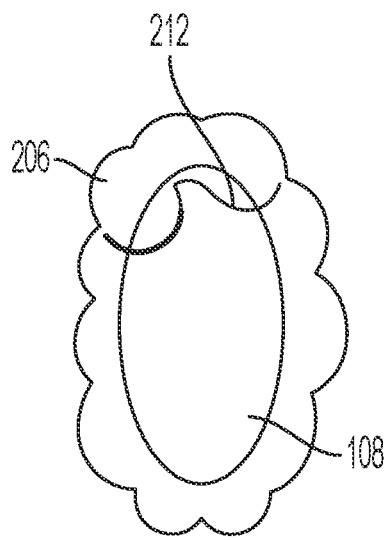
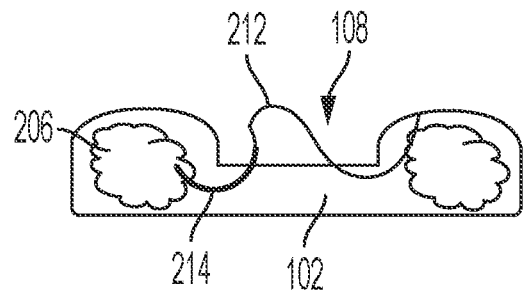
FIG. 3A    FIG. 3B
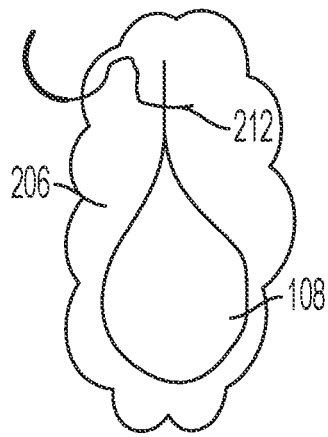
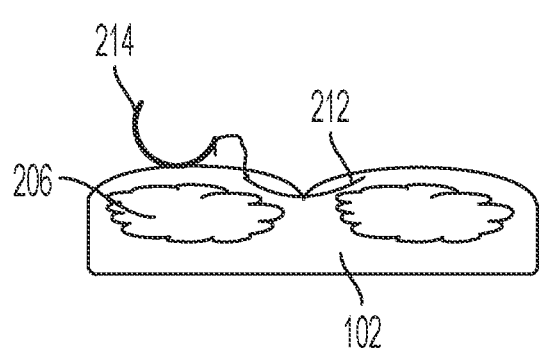
FIG. 3C    FIG. 3D
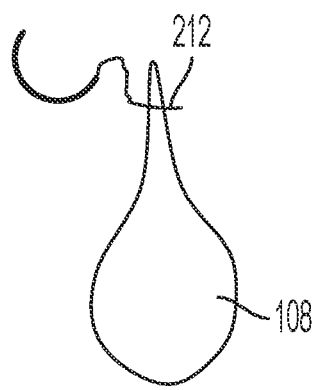
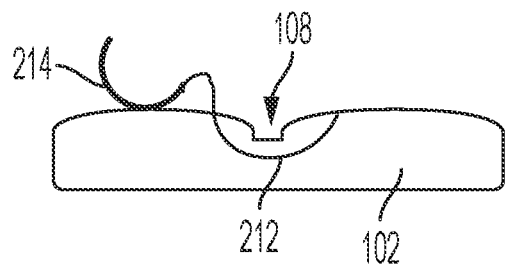
FIG. 3E    FIG. 3F

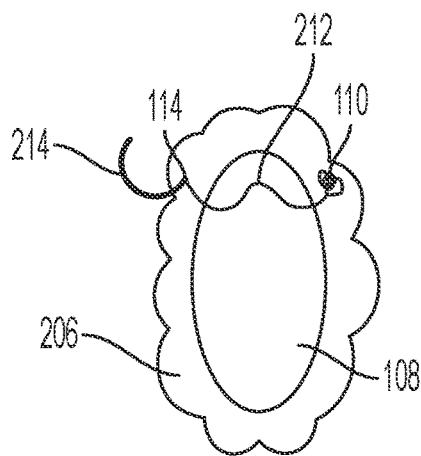
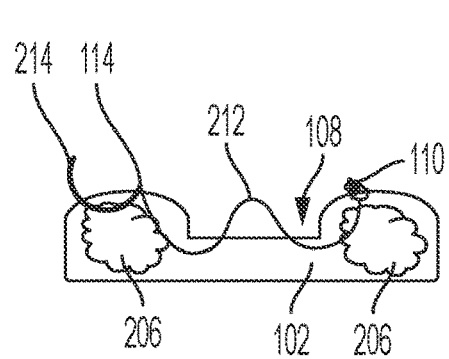
FIG. 4A                FIG. 4B
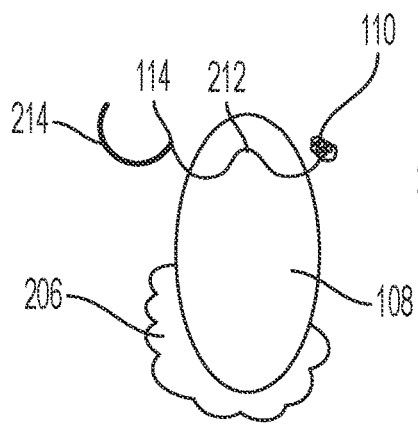
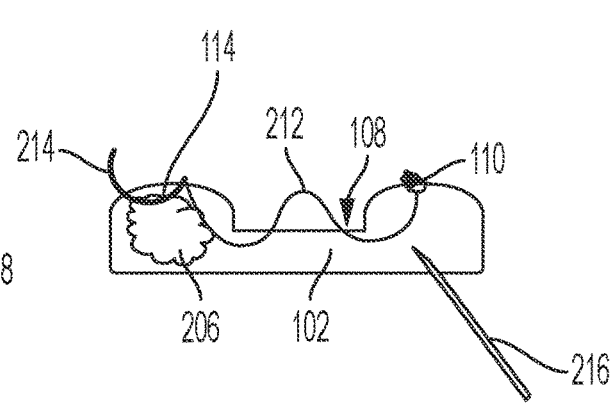
FIG. 4C                FIG. 4D
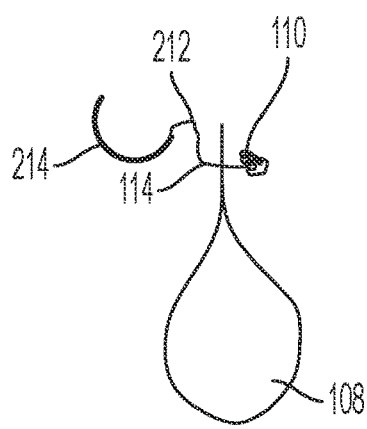
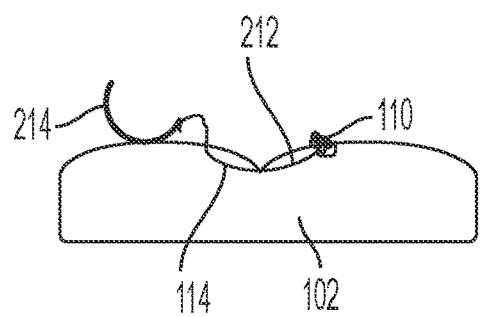
FIG. 4E                FIG. 4F

METHOD FOR CLOSING A WOUND

RELATED APPLICATION DATA

This application is based on and claims priority under 35 U.S.C. § 119 to U.S. Provisional Application No. 63/142,592, filed Jan. 28, 2021, the entire contents of which are incorporated herein by reference.

FIELD

The present disclosure, in certain embodiments, provides methods and apparatuses for resecting a lesion in a wall of an organ of a patient. In further embodiments, the present disclosure relates to methods and apparatuses for closing a wound. In some embodiments, methods and apparatuses of the present disclosure may be used to close wounds in the mucosal layer of a luminal organ of a patient. In some embodiments, methods and apparatuses of the present disclosure may be used to close wounds resulting from mucosectomy.

BACKGROUND

Mucosectomy is a surgical procedure that involves excising a portion of the mucous membrane from an organ of a patient, particularly along the gastrointestinal (GI) tract. Mucosectomy may be used, for example, to remove neoplasms, tumors, or other lesions from the internal wall of a luminal organ (e.g., esophagus, stomach, small intestine, colon, etc.). Two example mucosectomy techniques are endoscopic mucosal resection (EMR) and endoscopic submucosal dissection (ESD), each of which utilize endoscopy to excise certain lesions. EMR may be used to remove lesions located near the wall surface in the mucosa layer, whereas ESD may be suitable for removing deeper lesions that have not extensively penetrated the muscle layer of the organ wall.

Methods for EMR and/or ESD can generally include elevating the lesion away from the muscle layer, followed by resection of the elevated lesion. In some instances, elevating the lesion away from the muscle layer is achieved by injecting a bolus of fluid (e.g., a saline solution) into the submucosa beneath the lesion sufficient to separate the lesion from the muscle layer. For certain EMR procedures, resection may include positioning and tightening a snare loop around the elevated lesion and resecting the strangulated lesion using, for example, electrocautery. For certain ESD procedures, resection of the lesion may include circumferential cutting of the surrounding mucosa of the lesion and dissection of the connective tissue of the submucosa beneath the lesion.

Whether by EMR, ESD, or other mucosectomy procedure, the resection of the lesion creates a wound in the mucosal and/or submucosal layers where the lesion has been removed. The wound may be left open and allowed to heal on its own, however, this route presents a risk of infection and/or bleeding, and may be an unacceptable option for certain patients, such as patients receiving antithrombotic drugs or blood thinning agents. Thus, in other instances, it may be desirable to close the wound.

For some procedures, surgical clips may be employed to close the wound. Surgical clips, however, are limited by their size and therefore may be suitable only for closing relatively small wounds. Wounds may alternatively be closed by suturing. Such suturing techniques may include, for example, passing a suture thread between the mucosa layer on opposing sides of the wound, and tightening the suture thread in order to draw the opposing sides together to close the wound. However, it has been found that typical suturing techniques may suffer from certain drawbacks.

SUMMARY

A potential difficulty encountered with suturing the wound is the loosening of the suture thread over time, which may allow the wound to reopen. Reopening of the wound, even partially, can increase the risk for bleeding, infection, or other complications. Such loosening may occur, for example, if the tissue surrounding the wound changes shape to an extent that causes the suture thread to shift in position and/or slacken. Loosening of the suture thread can be a particular problem for wounds resulting from an EMR or ESD procedure since the mucosal and/or submucosal layers around the wound will contract as the fluid injected to elevate the lesion prior to resection dissipates from the wound site and/or is absorbed by the patient's body.

The present disclosure, according to some embodiments, provides methods for closing a wound that can overcome the problems discussed above. In some embodiments, a method of the present disclosure includes removing at least a portion of the fluid injected during a mucosectomy procedure (e.g., EMR or ESD procedures) prior to closing the resulting wound. In some embodiments, the removal of the injected fluid may occur before introducing a suture thread to close the wound. In some embodiments, removal of the injected fluid may occur after introduction of the suture thread, but prior to tightening of the suture thread to close the wound. In some embodiments, the injected fluid may be removed via suctioning by a hollow needle inserted into the tissue surrounding the wound. A syringe or other pumping device may be connected to a proximal end of the hollow needle that is configured to suction the fluid through the hollow needle. In further embodiments, the present disclosure provides a device that may be useful in the methods described herein. In some embodiments, the device includes both a hollow needle for suctioning the fluid and forceps for holding and manipulating a suture thread.

In some embodiments, the present disclosure provides methods for resecting a lesion in a wall of an organ of a patient. A method according to some embodiments includes injecting a fluid into the wall of the organ at a location proximate to the lesion, creating a wound in the wall of the organ by excising the lesion from the wall of the organ, removing at least a portion of the fluid injected into the wall of the organ, and closing the wound using a suture thread after removing the portion of fluid injected into the wall of the organ. In some embodiments, the lesion is located in a mucosal layer of the wall of the organ, and at least a portion of the fluid is injected into the wall of the organ beneath the lesion. In some embodiments, injecting the fluid elevates the lesion away from a muscle layer of the wall of the organ. In some embodiments, removing at least a portion of the fluid comprises removing at least 50% of the fluid injected into the wall of the organ.

In some embodiments, removing at least a portion of the fluid comprises inserting a distal end of a hollow needle into the wall of the organ, and suctioning the portion of the fluid from the wall of the organ through the hollow needle. A suctioning device (e.g., a syringe or pump) may be coupled to a proximal end of the hollow needle. In some embodiments, the hollow needle extends from a distal end of a device, the distal end of the device further comprising forceps configured to manipulate the suture thread. In some such embodiments, a proximal end of the device includes a control handle configured to transition the forceps between an open position and a closed position.

In some embodiments, prior to removing the portion of the fluid injected into the wall of the organ, the suture thread is threaded into the wall of the organ at a first position on a first side of the wound. In some embodiments, the suture thread is also threaded into the wall of the organ at a second position located on a second side of the wound opposite from the first side of the wound. In some embodiments, threading the suture thread into the wall of the organ at the second position occurs prior to removing the portion of the fluid injected into the wall of the organ. In some embodiments, threading the suture thread into the wall of the organ at the second position occurs after removing the portion of the fluid injected into the wall of the organ. In some embodiments, a method according to the present disclosure includes removing a second portion of the fluid injected into the wall of the organ after threading the suture thread into the wall of the organ at the second position. In other embodiments, removing at least a portion of the fluid injected into the wall of the organ occurs prior to threading the suture thread into the wall of the organ.

In further embodiments, the present disclosure provides a device for closing a wound. A device for closing a wound according to some embodiments includes an elongated shaft having a distal end and a proximal end, a hollow needle extending from the distal end of the shaft, the hollow needle having a distal end configured to be inserted into a tissue of a patient and a proximal end configured to be connected to a suctioning device (e.g., a syringe or pump). In some embodiments, the device further includes forceps positioned at the distal end of the shaft having an arm movable between an open configuration and a closed configuration, and a control handle positioned at the proximal end of the shaft, the control handle configured to transition the arm of the forceps between the open configuration and the closed configuration. In some embodiments, the arm is configured to hold a suture needle in the closed configuration. In some embodiments, the device further includes a mechanical linkage housed within the shaft connecting the control handle to the forceps. In some embodiments, the device includes a valve fitting in fluid communication with the proximal end of the hollow needle, the valve fitting configured to connect to the suctioning device. In some embodiments, the distal end of the hollow needle is retractable within the shaft.

BRIEF DESCRIPTION OF THE DRAWINGS

The foregoing summary, as well as the following detailed description, will be better understood when read in conjunction with the appended drawings. For the purpose of illustrating the present disclosure, there are shown in the drawings embodiments which are presently preferred, wherein like reference numerals indicate like elements throughout. It should be noted, however, that aspects of the present disclosure can be embodied in different forms and thus should not be construed as being limited to the illustrated embodiments set forth herein. The elements illustrated in the accompanying drawings are not necessarily drawn to scale, but rather, may have been exaggerated to highlight the important features of the subject matter therein. Furthermore, the drawings may have been simplified by omitting elements that are not necessarily needed for the understanding of the disclosed embodiments.

FIGS. 2A-2D illustrate a suturing method for closing a wound created by resecting a lesion from the wall of an organ, according to certain embodiments.

FIGS. 3A-3F illustrate the closing and reopening of a wound caused by fluid remaining in the surrounding tissue according to certain embodiments.

FIGS. 4A-4F illustrate the removal of fluid from the tissue surrounding the wound prior to closing the wound with suturing according to certain embodiments.

DETAILED DESCRIPTION

The present subject matter will now be described more fully hereinafter with reference to the accompanying Figures, in which representative embodiments are shown. The present subject matter can, however, be embodied in different forms and should not be construed as limited to the embodiments set forth herein. Rather, these embodiments are provided to describe and enable one of skill in the art.

Figures 1A, 1B, 1C:
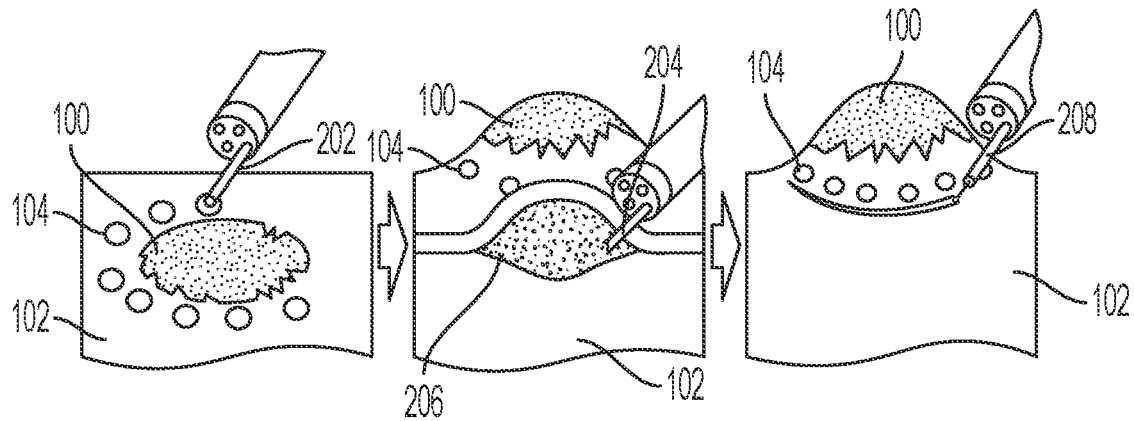
FIGS. 1A-1F illustrate steps for resecting a lesion from the wall of an organ of a patient according to certain example methods.

FIGS. 1A-1F illustrate steps of a mucosectomy procedure according to certain examples for resection of a lesion from an organ wall of a patient. The mucosectomy procedure may include, for example, an EMR procedure or an ESD procedure. The patient may be a human patient, or a non-human animal patient (e.g., a veterinarian patient). FIG. 1A shows a lesion 100 on a wall 102 of an organ of a patient, for example, a luminal organ of the GI tract (e.g., esophagus, stomach, small intestine, colon, etc.). Lesion 100 may be, for example, a benign tumor, cancerous tumor, or other abnormal growth that is present on the mucosa layer of wall 102. As further illustrated in FIG. 1A, a marking tool 202 (e.g., an endoscopic electric coagulator or cauterizer) may be used to create one or more markings 104 around lesion 100 in order to demarcate the boundary of lesion 100 for resection.

In FIG. 1B, an injection tool 204 (e.g. an endoscopic injection needle) is used to inject a fluid 206 into wall 102 beneath lesion 100. Fluid 206 may be an aqueous solution, for example, a saline solution or a hyaluronic acid solution. In some embodiments, fluid 206 is or includes a gel (e.g., hydrogels, thermogels, hydroxypropyl methylcellulose, poloxamer, etc.). Fluid 206 may further contain one or more pharmaceutically active agents (e.g., epinephrine). Fluid 206 may be injected into the submucosal layer of wall 102 beneath lesion 100, and may be injected through one or more injection sites around lesion 100. The amount of fluid 206 that is injected should be sufficient to elevate lesion 100 away from the muscle layer of wall 102 and cause lesion 100 to physically bulge from wall 102. In some embodiments, endoscopic images of lesion 100 and the surrounding tissue may be viewed to confirm sufficient elevation and bulging. The presence of wrinkles, for example, may indicate that bulging is insufficient and that additional fluid 206 may be needed. In some examples, about 40 mL to about 50 mL of fluid 206 may be administered via four or five syringes, each syringe containing about 10 mL of fluid 206. The amount of fluid 206 that is injected may be less or greater in other examples, depending on the size of lesion 100

Figures 1D, 1E, 1F:
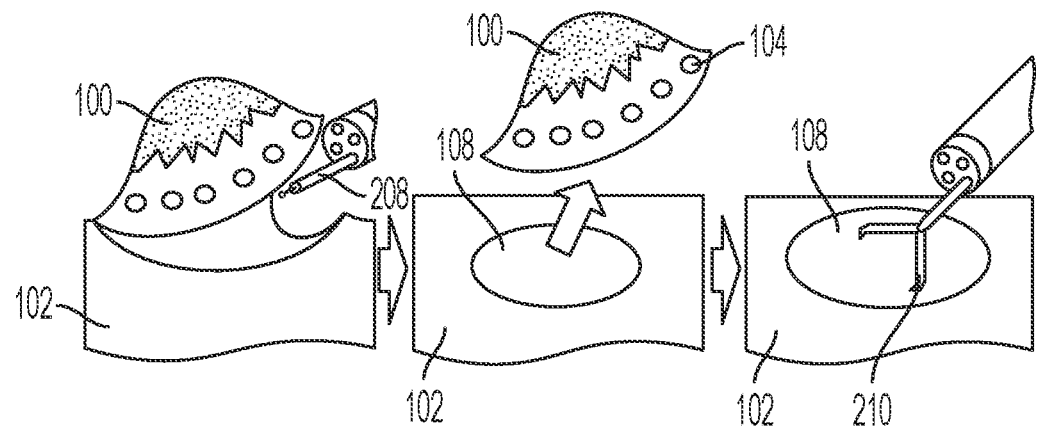

After lesion 100 is sufficiently elevated, lesion 100 may be excised from wall 102 as depicted in FIGS. 1C and 1D. A cutting tool 208 (e.g., an endoscopic electrosurgical knife) may be used to cut into the mucosal layer and/or submucosal layer of wall 102 around lesion 100. In some examples, cutting tool 208 is used to make a circumferential cut in the mucosal layer of wall 102 guided by or around the one or more markings 104. Dissection of connective tissues of the submucosa beneath lesion 100 may also be performed by cutting tool 208 in order to fully resect lesion 100 from wall 102.

FIG. 1E shows lesion 100 completely resected from wall 102. Lesion 100 may then be removed from the patient's body for pathological examination or disposal. The removal of lesion 100 leaves a wound 108 in wall 102 where lesion 102 was resected. Wound 108 may extend as deep as the mucosal layer or the submucosal layer of wall 102 according to some examples. Following removal of lesion 100, wound 108 may be closed to prevent bleeding, infection, or other complications. As shown in FIG. IF, in some examples one or more surgical clips 210 may be employed to close wound 108. As discussed, surgical clips 210 may be suitable for wounds that are relatively small in size. Thus, in some embodiments, wound 108 may alternatively be closed by suturing with a suture thread, as depicted in FIGS. 2A-2D, for example.

As shown in FIG. 2A, a suture thread 212 is provided for closing wound 108. Suture thread 212, in some embodiments, may be an absorbable suture thread and have a gauge of USP 3-0 or about 0.2 mm diameter, for example. In some embodiments, suture thread 212 may be a barbed suture thread. At a first end of suture thread 212 is a suture needle 214 for piercing the mucosal layer of wall 102 and guiding suture thread 212 there through.

Suture needle 214 may be, for example, a curved needle and may be manipulated by an endoscopic needle holder or forceps (not shown). A second end of suture thread 212 may be anchored in wall 102 at a first location 110 proximate to wound 108, for example, by one or more knots. In some embodiments, second end of suture thread 212 may include an eyelet through which suture needle 214 and the first end of suture thread 212 may be passed to form a loop for anchoring around a portion of the mucosa at first location 110.

To suture wound 108, in some embodiments, suture thread 212 is passed through the mucosal layer of wall 102 back and forth between opposite sides of wound 108 beginning from location 110, as illustrated in FIGS. 2B and 2C. Suture thread 212 may then be pulled tight to draw the opposing sides of wound 108 closed, and suture thread 212 may be anchored at a second location 112 in wall 102, e.g., by one or more knots, in order to prevent suture thread 212 from backing out. In some embodiments, wound 108 may be closed with a continuous stitch. In other embodiments, wound 108 may be closed by a series of separate stitches. Once the suturing is completed, suture needle 214 may be detached from suture thread 212, for example, by cutting suture thread 212 with a cutting tool (e.g., endoscopic cutting forceps) at a location between suture needle 214 and second location 112, as shown in FIG. 2D.

As discussed, a problem that may be encountered is that the suture thread can loosen over time, allowing the wound to reopen. This loosening may occur, for example, when the mucosal and/or submucosal layers surrounding the wound changes shape and causes the suture thread to shift in position. In some instances, as fluid 206 that is injected to elevate the lesion dissipates from the wound site and/or is absorbed by the patient's body, the tissue surrounding the wound may begin to contract and cause the suture thread to slacken. As a result, the wound may reopen leading to complications such as bleeding, infection, or other negative conditions.

FIGS. 3A-3F illustrate one effect that may arise from loosening of a suture thread in one such example. FIGS. 3A and 3B show wound 108 prior to closure by suture thread 212. As shown, a portion of injected fluid 206 (e.g., saline solution) remains in the mucosal and/or submucosal layers of wall 102 surrounding wound 108. FIGS. 3C and 3D depict wound 108 being closed by suture thread 212 with fluid 206 still present in the surrounding tissues of wall 102. As fluid 206 dissipates and/or is absorbed by the patient's body, the tissue around wound 108 may contract causing wound 108 to at least partially reopen, as shown in FIGS. 3E and 3F.

In order to avoid or decrease the possibility of the suture thread becoming loosened, methods according to embodiments of the present disclosure further include removing at least a portion of the injected fluid (e.g., fluid 206) prior to closing the wound. In some embodiments, removal of at least a portion of fluid 206 prior to closing the wound decreases the amount by which the tissues surrounding wound 108 may change shape after the wound is closed as a result of fluid 206 dissipating from the wound area or being absorbed by the patient's body. In some embodiments, at least a portion of fluid 206 is removed prior to inserting the suture thread into the tissue surrounding the wound. In some embodiments, at least a portion of fluid 206 is removed after inserting the suture thread into the tissue surrounding the wound, but prior to completing the stitching and/or prior to tightening the suture thread to close the wound. In some embodiments, fluid 206 may be removed by aspirating or suctioning fluid 206 from wall 102 after lesion 100 has been resected. In some embodiments, a needle is provided having a distal end configured to be inserted into wall 102 to remove fluid 206 from wall 102. In some embodiments, a suctioning device (e.g., syringe or other pump) may be connected to a proximal end of the needle and configured to suction fluid 206 from wall 102 through the needle.

FIGS. 4A-4F illustrate steps of a method according to some embodiments of the present disclosure where at least a portion of fluid 206 is removed from wall 102 prior to retracting the suture thread so as to bring portions of the boundary of the wound into contact with each other and closing wound 108. As shown in, FIGS. 4A and 4B suture thread 212 is passed at least once through opposing regions of wound 108 while some amount of fluid 206 remains in the mucosal and/or submucosal layers of wall 102 surrounding wound 108. In FIGS. 4C and 4D, after inserting suture thread 212, but prior to completely closing wound 108 with suture thread 212, at least a portion of fluid 206 is removed from wall 102. In some embodiments, a portion of fluid 206 may be removed from wall 102 in multiple steps. In some such embodiments, for example, a portion of fluid 206 may be removed after each pass of suture thread 212 between opposing sides of wound 108.

In some embodiments, prior to removing the portion of fluid 206, suture thread 212 is threaded into wall 102 at a first position on a first side of wound 108 (e.g., location 110). In some embodiments, suture thread 212 is further threaded through wall 102 at a second position 114 located on a second side of the wound opposite from the first side of the wound. In some embodiments, a first portion of fluid 206 may be removed from wall 102 before suture thread is threaded into wall 102 at second position 114, and a second portion of fluid 206 may be removed after suture thread is threaded into wall 102 at second position 114. In other embodiments, suture thread 212 may be threaded into first position (e.g., location 110) and second position 114 prior to removing any of fluid 206.

In some embodiments, fluid 206 is removed using a hollow needle 216 having a distal end that is inserted into one or more regions of wall 102 surrounding wound 108 and positioned to suction at least a portion of fluid 206 out of wall 102. In some embodiments, a proximal end of hollow needle 216 may be coupled to a syringe or other suctioning device (not shown) for supplying the suctioning force to draw fluid 206 out of wall 102 via hollow needle 216. In some embodiments, as much fluid 206 is removed from wall 102 as possible before closing wound 108. In some embodiments, at least 25% to at least 50% of the amount of fluid 206 that was injected into wall 102 is removed prior to closing wound 108. In some embodiments, at least 50% to at least 75% of the amount of fluid 206 that was injected into wall 102 is removed prior to closing wound 108. After fluid 206 has been removed from the tissue, hollow needle 216 is withdrawn and suture 212 may be pulled tight to draw the opposing regions of wound 108 together and close wound 108, as depicted in FIGS. 4E and 4F.

Figure 5A:
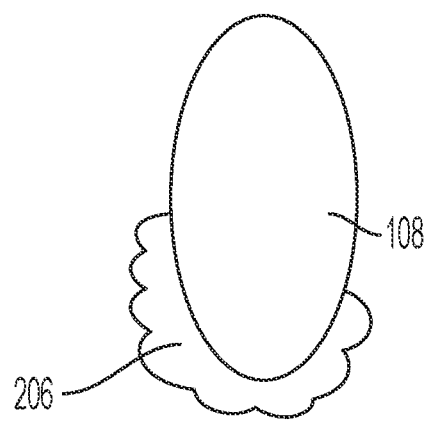
FIGS. 5A-5F illustrate the removal of fluid from the tissue surrounding the wound prior to closing the wound according to certain embodiments.
Figure 5B:
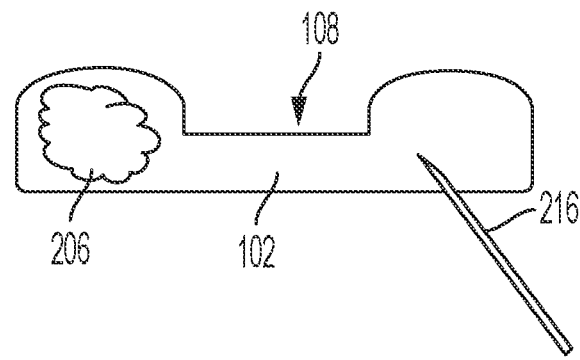
Figure 5C:
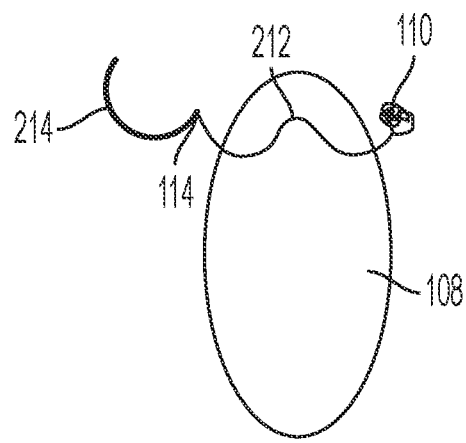
Figure 5D:
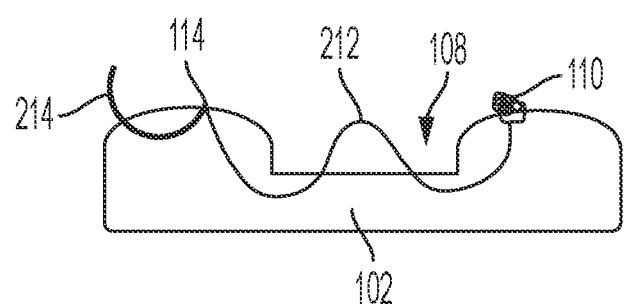
Figure 5E:
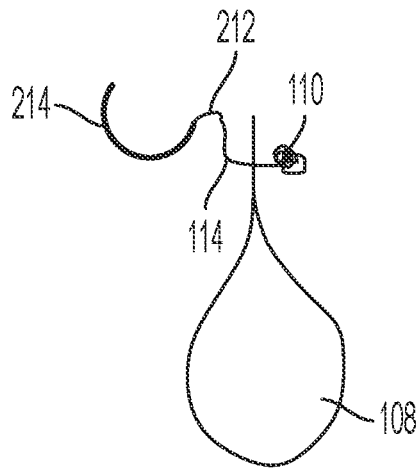
Figure 5F:
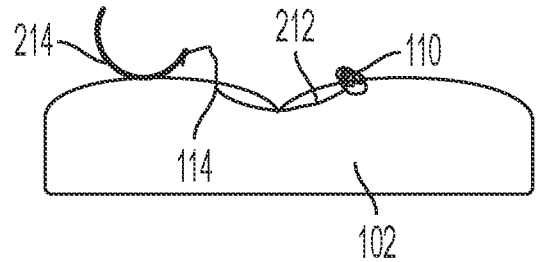

In other embodiments, fluid 206, or a portion thereof, may be removed from wall 102 prior to introducing suture thread 212, as shown FIGS. 5A-5F. As illustrated in FIGS. 5A and 5B, fluid 206 is removed using a hollow needle 216 before suture thread 212 is passed at least once through opposing regions of wound 108 (e.g., as described herein). As discussed in prior embodiments, hollow needle 216 may include a distal end that is inserted into one or more regions of wall 102 surrounding wound 108 and positioned to suction at least a portion of fluid 206 out of wall 102. A proximal end of hollow needle 216 may be coupled to a syringe or other suctioning device (not shown) for supplying the suctioning force to draw fluid 206 out of wall 102 via hollow needle 216. In some embodiments, as much fluid 206 is removed from wall 102 as possible before suturing wound 108. In some embodiments, at least 25% to at least 50% of the amount of fluid 206 that was injected into wall 102 is removed prior to suturing wound 108. In some embodiments, at least 50% to at least 75% of the amount of fluid 206 that was injected into wall 102 is removed prior to suturing wound 108. After a sufficient amount of fluid 206 has been removed from wall 102, hollow needle 216 may be withdrawn and suture thread 212 is passed between opposing regions of wound 108 (e.g., from location 110 to position 114), as shown in FIGS. 5C and 5D. In FIGS. 5E and 5F, suture thread 212 is pulled tight to draw the opposing regions of wound 108 together to contact each other and close wound 108.

Figure 6A:
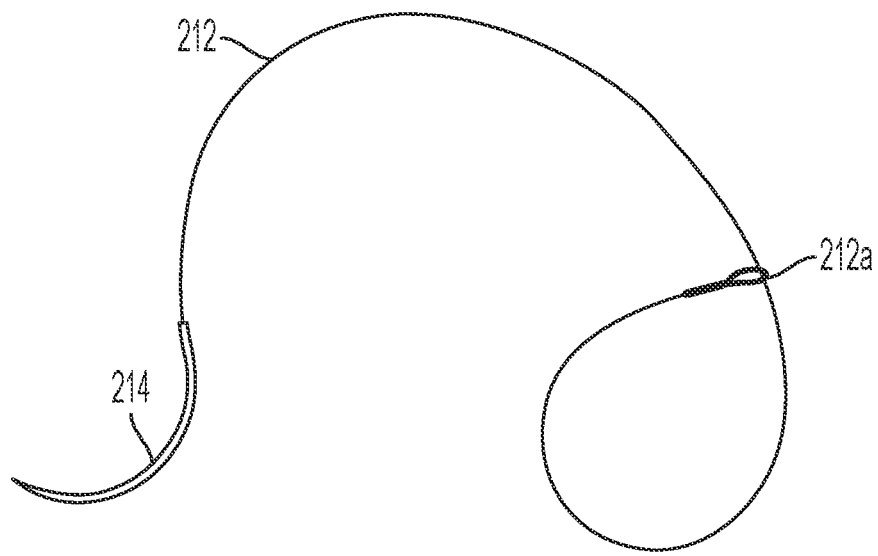
FIGS. 6A and 6B are photographs showing an example suture and suture needle that may be used according to certain embodiments.
Figure 6B:
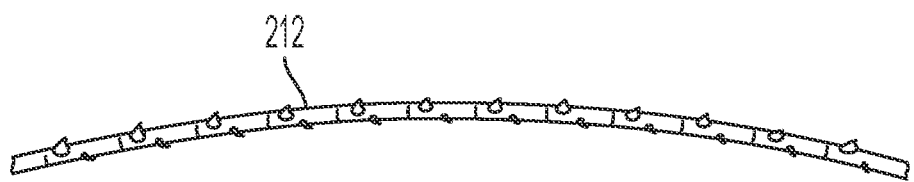

FIG. 6A shows an example suture thread 212 and suture needle 214 that may be used in accordance with some or each of the embodiments of the present disclosure. Suture thread 212 may be made from an bio-absorbable material and, in some embodiments, may include a plurality of barbs (visible in FIG. 6B) that are configured to help anchor suture thread 212 in wall 102 and reduce the need for tying knots. In further embodiments, suture thread 212 may include an eyelet 212a at the end opposite of suture needle 214. In some such embodiments, suture needle 214 may be passed through eyelet 212a to form a loop that may be used for anchoring suture thread 212 to wall 102.

Figure 7:
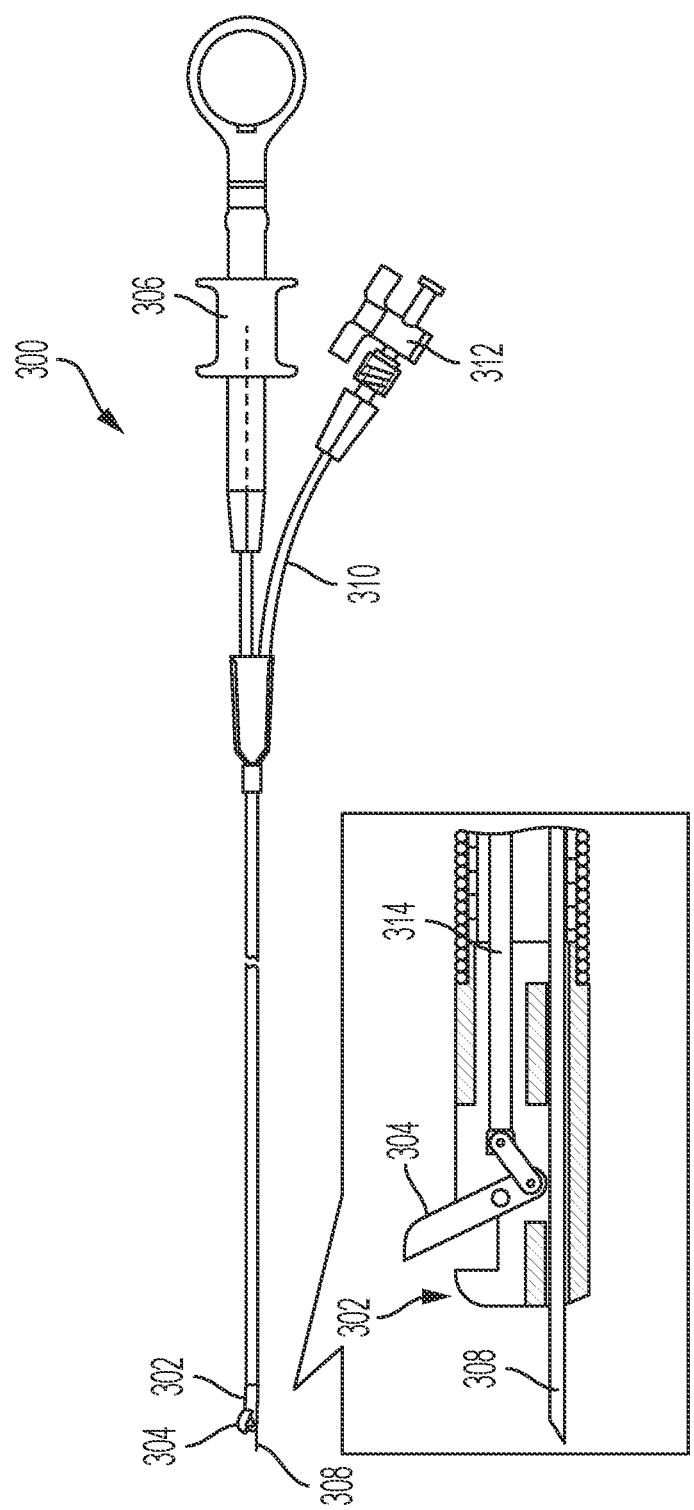
FIG. 7 shows a device having a combination of forceps for manipulating a suture and a hollow needle for suctioning of fluid from tissue that may be useful in the methods described herein according to certain embodiments.

In some embodiments, the hollow needle for suctioning fluid 206 may be combined with a suturing tool in a single device. In some embodiments, such a device may be conveniently used for performing both the removal of fluid 206 and the suturing of wound 108. One such example device is illustrated in FIG. 7 and generally designated 300. Device 300 may be configured for endoscopic use according to some embodiments and includes an elongated shaft having a distal end 302 sized to be inserted into the body of a patient. In some embodiments, device 300 includes forceps 304 located at distal end 302 and configured for holding and manipulating a suture needle (e.g., suture needle 214). Forceps 304 may include a movable arm configured to hold or clamp the suture needle, which may be controlled by a control handle 306 located at a proximal end of device 300. Control handle 306 may operate to open or close forceps 304 by causing the movable arm to pivot between open and closed positions. For example, in some embodiments, control handle 306 may be connected to the movable arm by a mechanical linkage 314 housed within the shaft that is configured to transmit mechanical force or energy from control handle 306 to forceps 304, e.g., a rod or Bowden cable.

Device 300, in some embodiments, further includes a hollow needle 308 extending from distal end 302 and configured to be inserted into the tissue of the patient. Hollow needle 308 may be used similarly as hollow needle 216 described previously to suction fluid away from the tissue (e.g., fluid 206). In some embodiments, hollow needle 308 is at least partially housed within the shaft of device 300 and includes a distal end configured to be inserted into wall 102 and a proximal end opposite the distal end configured to be in fluid communication with a suctioning device (e.g., syringe or pump). In some embodiments, the proximal end of hollow needle 308 may be in fluid communication with tubing 310 and fitting 312 at the proximal end of device 300. Fitting 312 may include, for example, a valve or cock and be configured to attach to a syringe or other suctioning device for drawing fluid through hollow needle 308. In some embodiments, distal end of hollow needle 308 may be retracted into the shaft of device 300 when not in use.

While certain embodiments of the present disclosure have been described in connection with certain EMR or ESD procedures, the methods and devices described herein are not necessarily limited to these procedures. Methods and devices according to some embodiments that are useful for closing wounds may be adapted for use with other mucosectomy procedures or other medical procedures which result in a wound. Furthermore, the methods and devices described herein are not necessarily limited for use in the GI tract of a patient, and may be adapted for use in other luminal organs, for example, organs of the respiratory system (e.g., trachea), circulatory system (e.g., veins or arteries), urinary tract (e.g., bladder), reproductive tract (e.g., uterus), etc.

It should be understood that various changes, substitutions, and alterations can be made herein without departing from the spirit and scope of the invention as defined by the appended claims. It should also be apparent that individual elements identified herein as belonging to a particular embodiment may be included in other embodiments of the invention. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, composition of matter, means, methods, or steps, presently existing or later to be developed that perform substantially the same function or achieve substantially the same result as the corresponding embodiments described herein may be used according to the present disclosure.

What is claimed is:

1. A method for closing a wound of an organ of a patient, the method comprising:
   injecting a liquid solution into a submucosal layer of a wall of the organ beneath a lesion so that the injected liquid solution elevates the lesion away from a muscle layer of the wall of the organ, the lesion being located in a mucosal layer of the wall of the organ;
   creating the wound in the wall of the organ by incising the submucosal layer to remove the lesion from the wall of the organ;
   removing the injected liquid solution contained within the wall of the organ in the submucosal layer outside of the wound after completely removing the lesion from the wall of the organ.

2. The method of claim 1, wherein removing the liquid solution comprises removing at least 50% of the liquid solution injected into the submucosal layer of the wall of the organ.

3. The method of claim 1, wherein removing the injected liquid solution comprises inserting a distal end of a hollow needle into the wall of the organ, and suctioning the liquid solution contained within the wall of the organ through the hollow needle.

4. The method of claim 3, wherein the hollow needle extends from a distal end of a device, the distal end of the device further comprising forceps configured to manipulate a suture thread.

5. The method of claim 1, further comprising:
   threading a suture thread into the wall of the organ at a first position on a first side of the wound and at a second position located on a second side of the wound opposite from the first side of the wound; and
   retracting the suture thread so that the first side of the wound and the second side of the wound contact each other.

6. A method for treatment, the method comprising:
   injecting a liquid solution into a submucosal layer of a wall of an organ beneath a lesion so that the injected liquid solution elevates the lesion away from a muscle layer of the wall of the organ, the lesion being located in a mucosal layer of the wall of the organ;
   incising the submucosal layer to remove the lesion from the wall of the organ, wherein incising the submucosal layer creates a wound in the wall of the organ; and
   removing the injected liquid solution contained within the wall of the organ in the submucosal layer outside of the wound after completely removing the lesion from the wall of the organ.

7. The method of claim 6, wherein removing the injected liquid solution comprises removing at least 50% of the injected liquid solution injected into the wall of the organ.

8. The method of claim 6, wherein removing the injected liquid solution comprises inserting a distal end of a hollow needle into the wall of the organ, and suctioning the injected liquid solution from the wall of the organ through the hollow needle.

9. The method of claim 8, wherein a suctioning device is coupled to a proximal end of the hollow needle.

10. The method of claim 9, wherein the suctioning device comprises a syringe.

11. The method of claim 6, further comprising:
    threading a suture thread into the wall of the organ at a first position on a first side of the wound and at a second position located on a second side of the wound opposite from the first side of the wound before removing the injected liquid solution contained within the wall of the organ in the submucosal layer outside of the wound; and
    retracting the suture thread so that the first side of the wound and the second side of the wound contact each other after removing the injected liquid solution contained within the wall of the organ in the submucosal layer outside of the wound.

12. The method of claim 11, wherein removing injected liquid solution comprises inserting a distal end of a hollow needle into the wall of the organ and suctioning the injected liquid solution from the wall of the organ through the hollow needle, and
    wherein the hollow needle extends from a distal end of a device, the distal end of the device further comprising forceps configured to manipulate the suture thread.

13. The method of claim 6, further comprising:
    threading a suture thread into the wall of the organ at a first position on a first side of the wound and at a second position located on a second side of the wound opposite from the first side of the wound after removing the injected liquid solution contained within the wall of the organ in the submucosal layer outside of the wound; and
    retracting the suture thread so that the first side of the wound and the second side of the wound contact each other.

14. The method of claim 6, further comprising:
    threading a suture thread into the wall of the organ at a first position on a first side of the wound before removing the injected liquid solution contained within the wall of the organ in the submucosal layer outside of the wound;
    threading the suture thread into the wall of the organ at a second position located on a second side of the wound opposite from the first side of the wound after removing the injected liquid solution contained within the wall of the organ in the submucosal layer outside of the wound; and
    retracting the suture thread so that the first and the second sides of the wound contact each other.

15. A method for treatment, the method comprising:
    injecting a liquid solution into a submucosal layer beneath a portion of a mucosal layer of a wall of an organ of a patient;
    incising the submucosal layer to remove the portion of the mucosal layer from the organ, wherein incising the submucosal layer creates a wound in the wall of the organ; and
    removing the injected liquid solution contained within the wall of the organ in the submucosal layer outside of the wound after completely removing the portion of the mucosal layer from the organ.

16. The method of claim 15, wherein removing the liquid solution comprises removing at least 50% of the liquid solution injected into the submucosal layer.

17. The method of claim 15, wherein removing the injected liquid solution comprises inserting a distal end of a hollow needle into the wall of the organ, and suctioning the injected liquid solution from the wall of the organ through the hollow needle.

18. The method of claim 17, wherein the hollow needle extends from a distal end of a device, the distal end of the device further comprising forceps configured to manipulate a suture thread.

19. The method of claim 15, further comprising:
threading a suture thread into the wall of the organ at a first position on a first side of the wound and at a second position located on a second side of the wound opposite from the first side of the wound before removing the injected liquid solution contained within the wall of the organ in the submucosal layer outside of the wound; and
retracting the suture thread so that the first side of the wound and the second side of the wound contact each other after removing the injected liquid solution contained within the wall of the organ in the submucosal layer outside of the wound.

20. The method of claim 15, further comprising:
threading a suture thread into the wall of the organ at a first position on a first side of the wound and at a second position located on a second side of the wound opposite from the first side of the wound after removing the injected liquid solution contained within the wall of the organ in the submucosal layer outside of the wound; and
retracting the suture thread so that the first side of the wound and the second side of the wound contact each other.

21. The method of claim 15, further comprising:
threading a suture thread into the wall of the organ at a first position on a first side of the wound before removing the injected liquid solution contained within the wall of the organ in the submucosal layer outside of the wound;
threading the suture thread into the wall of the organ at a second position located on a second side of the wound opposite from the first side of the wound after removing the injected liquid solution contained within the wall of the organ in the submucosal layer outside of the wound; and
retracting the suture thread so that the first and the second sides of the wound contact each other.

* * * * *